US00PP09325P

United States Patent [19]

Zary

[11] Patent Number: Plant 9,325

[45] Date of Patent: Oct. 17, 1995

[54] MINIATURE ROSE PLANT 'JACREDEM'

[75] Inventor: Keith W. Zary, Thousand Oaks, Calif.

[73] Assignee: Bear Creek Gardens, Inc., Medford, Oreg.

[21] Appl. No.: 366,245

[22] Filed: Dec. 28, 1994

[51] Int. Cl.[6] ..... A01H 5/00

[52] U.S. Cl. ..... Plt./10

[58] Field of Search ..... Plt./7.1, 10

*Primary Examiner*—Howard J. Locker

*Attorney, Agent, or Firm*—Klarquist Sparkman Campbell Leigh & Whinston

[57] ABSTRACT

A miniature rose plant characterized by its small, dark red flowers produced freely and in small clusters; its vigorous, compact, well-branched habit of growth; its excellent disease resistance; and its small, dark green, glossy foliage.

1 Drawing Sheet

The present invention relates to a new and distinct variety of rose plant of the miniature class which was originated by me by crossing an unnamed seedling, unpatented, with an unnamed seedling, unpatented.

The primary objective of this breeding was to produce a new rose variety having the excellent flower production, dark green healthy foliage and vigorous, upright growth of the pink floribunda female combined with the deep red miniature flowers; small, glossy foliage, and health of the male parent. The objective was substantially achieved along with other desirable improvements, as evidenced by the following unique combination of characteristics that are outstanding in the new variety and that distinguish it from its parents, as well as from all other varieties of which I am aware:

1. Small, dark red flowers;
2. Small, glossy, dark green foliage;
3. Excellent disease resistance;
4. Vigorous, upright, compact habit of growth; and
5. Flowers produced freely and in small clusters.

Asexual reproduction of this new variety by softwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in a garden environment in Somis, Calif., from June through October 1994.

Blooming habit: Continuous.

Bud:

*Size.*—½ when the petals start to unfurl.

*Form.*—Short, pointed ovoid.

*Color.*—When sepals first divide, bud color is Red Group 44A with the lower third of petal flecked red and white. The very base of the petal is Yellow Group 2C. When half blown, the upper sides of the petals are Red Group 44A; and the lower sides of the petals are Red Group 44A flecked on a pinkish background.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 137C. Shape: Funnel. Size. Small, ⅛ inch by 3/16 inch. Surface: Smooth.

*Peduncle.*—Length: 1 to 1¼ inches. Surface: Smooth. Color: Medium green and bronzy when exposed to the sun. Strength: Stiff, erect, slender.

Bloom:

*Size.*—Small. Average open size is 1½ inches.

*Borne.*—Several together in groups of 3 to 7. Clusters: Pyramidal.

*Stems.*—Short (4 to 6 inches), strong.

*Form.*—When first open: High centered. Permanence: Retains its form to the end, outer petals curl back.

*Petalage.*—Number of petals under normal conditions: 30.

*Color.*—The upper side of the petals is Red Group 44A. The reverse side of the petals is Red Group 44A flecked on a pinkish background. The color of the base of petals is Yellow Group 2C. The major color on the upper side is Red Group 44A.

*Variegations.*—None.

*Discoloration.*—The general tonality at the end of the first and third days: No change.

*Fragrance.*—Slight.

Petals:

*Texture.*—Thick, leathery.

*Shape.*—Deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: 5 to 7 days. As a cut flower: 8 to 9 days.

Reproductive parts:

*Anthers.*—Size: Small. Quantity: Many. Color: Yellow. Arrangement: Regular around styles.

*Filaments.*—Color: Yellow.
*Pollen.*—Color: Lemon yellow.
*Styles.*—Color: Red.
*Stigmas.*—Color: Greenish white.

Form: Bush.

Growth: Vigorous, dwarf, upright, branching, compact. Will reach height of 20 to 24 inches in one season of growth.

Foliage: Number of leaflets on normal mid-stem leaves: 5 or 7.
*Size.*—Small (2½× 1½ inches).
*Quantity.*—Abundant.
*Color.*—New foliage: Greyed-Purple Group 183B. Old foliage: Upper side: Green Group 137A. Lower side: Green Group 139C.

Leaflets:
*Shape.*—Pointed oval.
*Texture.*— Upper side: Leathery, glossy.
*Edge.*—Serrated.
*Serration.*—Single, small.
*Petiole rachis.*—Color: Green.
*Petiole underside.*—Rough, with prickles.
*Stipules.*—Short (¼ inch), bearded.
*Disease resistance.*—Resistant to mildew and rust under normal growing conditions at Somis, Calif.

Wood:
*New wood.*—Color: Light green with some reddish coloration. Bark: Smooth.
*Old wood.*—Color: Green. Bark: Smooth.

Prickles:
*Quantity.*—On main canes from base: Ordinary. On laterals from main canes: Ordinary.
*Form.*—Short, straight to hooked slightly downward.
*Color when young.*—Red.

Small prickles:
*Quantity.*—On main stalks: Few. On laterals: Few.
*Color.*—Green.

I claim:

1. A new and distinct variety of rose plant of the miniature class, substantially as herein shown and described, characterized particularly as to novelty by the unique combination of its small, dark red flowers produced freely and in small clusters; its vigorous, compact, well-branched habit of growth; its excellent disease resistance; and its small, dark green, glossy foliage.

* * * * *

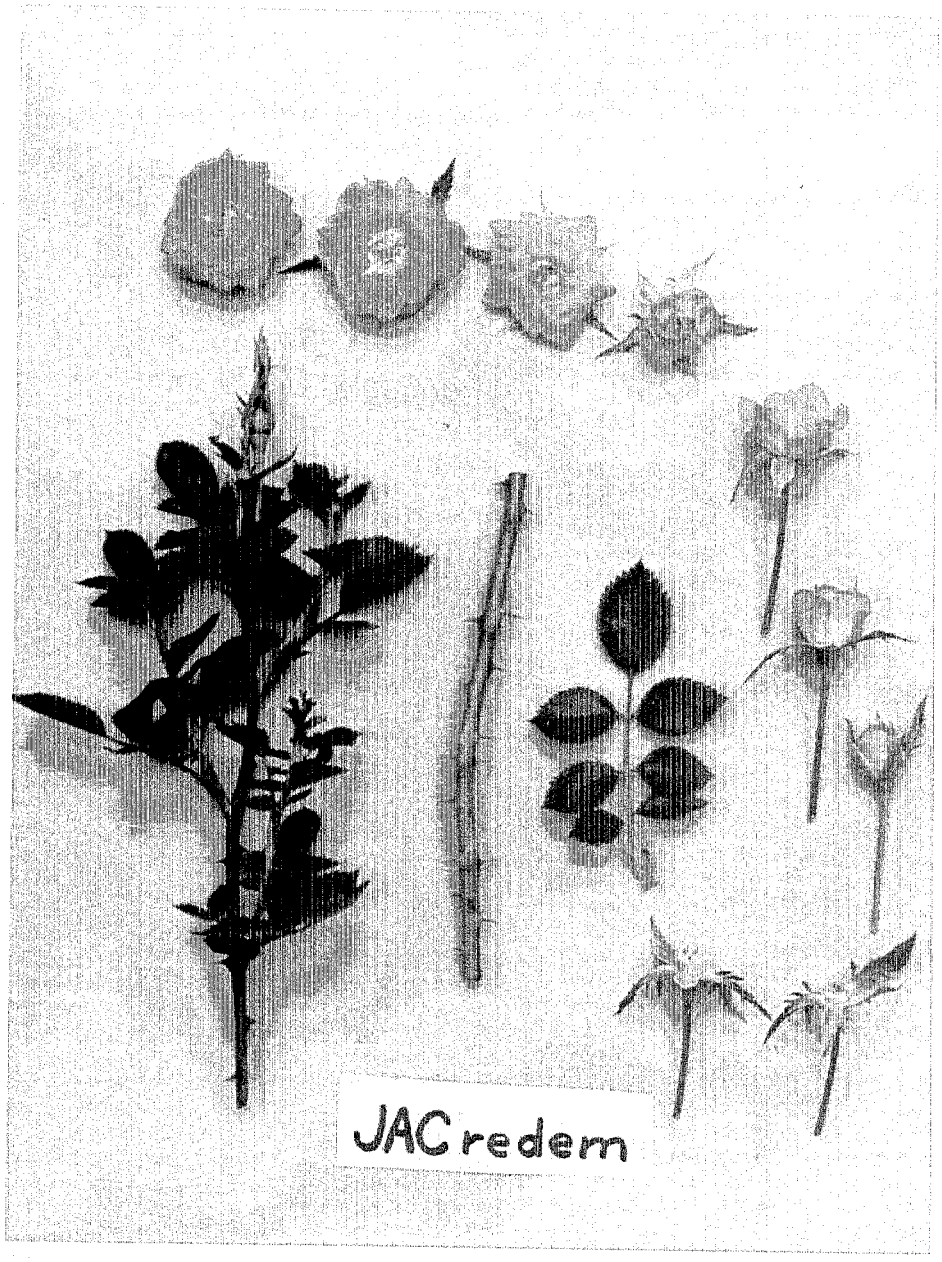
JAC redem